(12) United States Patent
Brooks et al.

(10) Patent No.: US 9,890,208 B2
(45) Date of Patent: Feb. 13, 2018

(54) COMPOSITIONS AND METHODS FOR TREATING INFLAMMATION AND FIBROSIS

(71) Applicant: Maine Medical Center, Scarborough, ME (US)

(72) Inventors: Peter C. Brooks, Harpswell, ME (US); Leif Oxburgh, South Portland, ME (US); Jennifer M. Caron, Scarborough, ME (US)

(73) Assignee: Maine Medical Center, Scarborough, ME (US)

( * ) Notice: Subject to any disclaimer, the term of this patent is extended or adjusted under 35 U.S.C. 154(b) by 32 days.

(21) Appl. No.: 14/488,753

(22) Filed: Sep. 17, 2014

(65) Prior Publication Data

US 2015/0010552 A1 Jan. 8, 2015

Related U.S. Application Data

(63) Continuation of application No. 13/395,373, filed as application No. PCT/US2010/052642 on Oct. 14, 2010.

(60) Provisional application No. 61/253,211, filed on Oct. 20, 2009.

(51) Int. Cl.
| | |
|---|---|
| *A61K 39/395* | (2006.01) |
| *C07K 16/18* | (2006.01) |
| *C07K 7/06* | (2006.01) |
| *A61K 39/00* | (2006.01) |

(52) U.S. Cl.
CPC ............ *C07K 16/18* (2013.01); *C07K 7/06* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,566,770 B2 | 7/2009 | Watkins et al. | |
| 7,588,760 B2 | 9/2009 | Brooks et al. | |
| 7,763,247 B2 | 7/2010 | Watkins et al. | |
| 8,025,883 B2 | 9/2011 | Brooks et al. | |
| 2003/0113331 A1 | 6/2003 | Brooks et al. | |
| 2004/0018186 A1 | 1/2004 | Denholm et al. | |
| 2004/0242490 A1 | 12/2004 | Brooks et al. | |
| 2005/0281821 A1* | 12/2005 | Pernasetti | A61K 31/00 424/155.1 |
| 2006/0088540 A1 | 4/2006 | Brooks et al. | |
| 2007/0048325 A1* | 3/2007 | Van Epps | A61K 38/10 424/155.1 |
| 2007/0077199 A1 | 4/2007 | Watkins et al. | |
| 2008/0008707 A1 | 1/2008 | Freimark et al. | |
| 2009/0028867 A1 | 1/2009 | Brooks et al. | |
| 2010/0226852 A1 | 9/2010 | Brooks et al. | |
| 2010/0266646 A1* | 10/2010 | Dvorak | A61K 8/731 424/401 |

FOREIGN PATENT DOCUMENTS

WO  WO-2007146401 A1  12/2007

OTHER PUBLICATIONS

Micromet 2007 Annual Report. May 5, 2008. pp. 1-157.*
Roth et al. Targeting the HU177 cryptic collagen epitope with humanized antibody TRC093 functions cooperatively with anti-VEGF therapy to inhibit tumor growth. AACR Annual Meeting—Apr. 18-22, 2009. Abstract #317.*
Brooks et al. Ionizing Radiation Modulates the Exposure of the HUIV26 Cryptic Epitope Within Collagen Type IV During Angiogenesis. Int. J. Radiation Oncology Biol. Phys., vol. 54, No. 4, pp. 1194-1201, 2002.*
Freimark et al. Targeting of humanized antibody D93 to sites of angiogenesis and tumor growth by binding to multiple epitopes on denatured collagens. Molecular Immunology 44 (2007) 3741-3750.*
Pernasetti et al. Novel anti-denatured collagen humanized antibody D93 inhibits angiogenesis and tumor growth: An extracellular matrix-based therapeutic approach. International Journal of Oncology 29: 1371-1379, 2006.*
De Laat et al. Carcinogenesis induced by UVA (365 nm) radiation: the dose-time dependence of tumor formation in hairless mice. Carcinogenesis 1997;18(5):1013-20.*
Lymberis et al. Inhibition of HU177 cryptic epitope within collagen enhances the antiproliferative effects of ionizing radiation in B16 melanoma. International Journal of Radiation Oncology Biology Physics, (2003) vol. 57, No. 2 Supplement, pp. S257-S258.*
Ng et al. Shedding of Distinct Cryptic Collagen Epitope (HU177) in Sera of Melanoma Patients. Clin Cancer Res. Oct. 1, 2008; 14(19): 6253-6258.*
D'Angelo et al. Hydroxytyrosol, a natural antioxidant from olive oil, prevents protein damage induced by long-wave ultraviolet radiation in melanoma cells. Free Radical Biology & Medicine 38 (2005) 908-919.*
FDA—Tanning > Ultraviolet (UV) Radiation pp. 1-7, (printed Jun. 13, 2017).*
Ames et al. Regulation of ovarian tumor growth and stromal cell infiltration by the HU177 biomechanical ECM switch. Cancer Research: Apr. 15, 2012; vol. 72, Issue 8, Supplement 1, Proceedings: AACR 103rd Annual Meeting 2012—Mar. 31-Apr. 4, 2012; Chicago, IL. Abstract 1480.
Cretu et al. Disruption of Endothelial Cell Interactions with the Novel HU177 Cryptic Collagen Epitope Inhibits Angiogenesis Clin Cancer Res 2007;13:3068-3078.

* cited by examiner

*Primary Examiner* — Maher M Haddad

(74) *Attorney, Agent, or Firm* — Mintz Levin Cohn Ferris Glovsky and Popeo, P.C.

(57) ABSTRACT

The present invention features compositions featuring agents that bind to denatured collagen and methods of using such agents to treat or prevent fibrosis or inflammation in a subject.

10 Claims, 8 Drawing Sheets

Figure 1C & D.
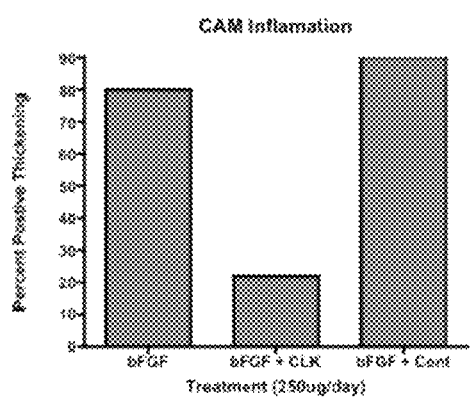
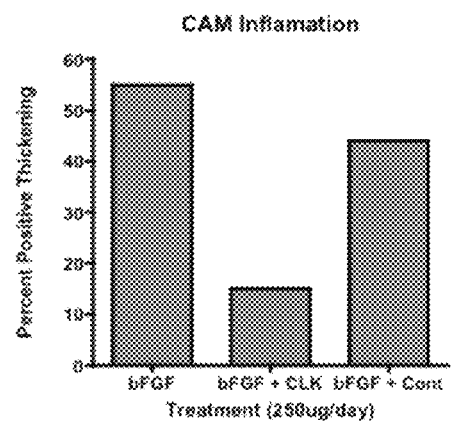

COMPOSITIONS AND METHODS FOR TREATING INFLAMMATION AND FIBROSIS

CROSS-REFERENCE TO RELATED APPLICATION

This application is a continuation of U.S. application Ser. No. 13/395,373 filed May 29, 2012 (now abandoned), which is a U.S. national phase application of PCT/US2010/052642, filed Oct. 14, 2010, which claims the benefit of U.S. Provisional Application No. 61/253,211, filed Oct. 20, 2009, the entire contents of which are expressly incorporated herein by reference.

STATEMENT OF RIGHTS TO INVENTIONS MADE UNDER FEDERALLY SPONSORED RESEARCH

This invention was made with government support under grant number CA091645-08 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 17, 2012, is named 84927307.txt and is 3,153 bytes in size.

BACKGROUND OF THE INVENTION

It has been estimated that nearly 45% of all deaths in the United States and developing countries are associate with fibroproliferative diseases and inflammation. A wide range of human diseases and disorders are associated with uncontrolled infiltration of inflammatory cells such as monocytes, macrophages, neutrophils, and mast cells, which populate tissue sites of bacterial and viral infections, as well as sites of tissue damage caused by environmental toxins, chemicals, irradiation and mechanical trauma. Distinct inflammatory cell types, along with other cells such as activated fibroblasts, are well known to play critical roles in many human pathologies. In large part due to the multifactorial nature of inflammation and fibrosis, progress has been slow in the development of less toxic and more efficacious treatments for this large group of highly debilitating and often lethal diseases. While drugs have been developed that target individual molecules such as inflammatory cytokines, growth factors, enzymes, and their cognate receptors, many of these anti-inflammatory compounds are only marginally effective due to the diversity of molecules that contribute to these processes. Moreover, some of these anti-inflammatory drugs have side effects limiting their use.

Thus, there remains a need to develop safer and more efficacious approaches for the treatment of inflammation and fibrosis.

SUMMARY OF THE INVENTION

The present invention generally features compositions and methods featuring agents that bind to denatured collagen (e.g., collagen type I-IV) and methods of using such agents for the treatment or prevention of inflammation and/or fibrosis.

In one aspect, the invention provides a method of reducing fibrosis or inflammation in a subject (e.g., mammal, such as a human) in need thereof, the method involving administering to the subject a therapeutically effective amount of an agent that binds denatured collagen (e.g., any of types I-IV), wherein the agent is any one or more of proteins, peptides, antibodies, aptamers, oligopeptides, and small molecule inhibitors. In one embodiment, the agent reduces the infiltration of one or more types of inflammatory cells to a site in said subject.

In another aspect, the invention provides a method of reducing inflammatory cell infiltration of a site in a subject in need thereof, the method involving administering to the subject a therapeutically effective amount of an agent that binds denatured collagen type I-IV (e.g., denatured collagen type-IV), wherein the agent is any one or more of proteins, peptides, antibodies, aptamers, oligopeptides and small molecule inhibitors.

In another aspect, the invention provides a method of preventing or reducing ultraviolet radiation damage, ionizing radiation damage, or chemotherapy damage to a cell, tissue, or organ, the method involving administering to the subject a therapeutically effective amount of an agent that binds denatured collagen type I-IV (e.g., denatured collagen type-IV), wherein the agent is any one or more of proteins, peptides, antibodies, aptamers, oligopeptides and small molecule inhibitors.

In another aspect, the invention provides a kit for use in reducing inflammatory cell infiltration into a site comprising an agent that binds denatured collagen type I-IV (e.g., denatured collagen type-IV), and instructions for use.

In another aspect, the invention provides a kit for use in treating or preventing fibrosis or inflammation in a subject, the kit comprising an agent that binds denatured collagen type I-IV (e.g., denatured collagen type-IV), and instructions for use.

In various embodiments of any of the above aspects, the site is not a tumor site or other neoplastic tissue. In still other embodiments of the above aspects, the inflammatory cell is any one or more of monocytes, macrophages, neutrophils and mast cells. In still other embodiments of the above aspects, the agent reduces inflammatory cell infiltration to a site. In still other embodiments of the above aspects, the agent reduces adhesion to extracellular matrix or basement membrane. In still other embodiments of the above aspects, the agent reduces fibroblast cell adhesion to denatured collagen type I-IV. In still other embodiments of the above aspects, the agent is administered prior to, concurrent with, or subsequent to UVA radiation or ionizing radiation exposure or prior to chemotherapy. In still other embodiments of the above aspects, the site is the site of a bio-implant. In still other embodiments of the above aspects, the agent is an antibody or a monoclonal antibody, such as a humanized antibody. In still other embodiments of the above aspects, the agent specifically binds to an epitope of denatured collagen (e.g., collagen types I-IV). In still other embodiments of the above aspects, the agent specifically binds to an epitope of anti-denatured collagen type-IV comprising GLGP (SEQ ID NO: 2), GLGPGP (SEQ ID NO: 3), or OGAKGLPGPOGPOGPY (SEQ ID NO: 1). In still other embodiments of the above aspects, the agent is any one or more of L-K-Q-N-G-G-N-F-S-L (SEQ ID NO: 4), L-G, S-L-K-Q-N-G-G-N-F-S-L (SEQ ID NO: 5), C-L-K-Q-N-G-G-N-F-S-L-G (SEQ ID NO: 6), S-L-K-Q-N-G-G-N-F-S-L-C (SEQ ID NO: 6) and K-G-G-C-L-K-Q-N-G-G-N-F-S-L-G-G-K (SEQ ID NO: 8). In still other embodiments of the above aspects, the subject has a condition selected from the group consisting of pulmonary fibrosis, liver fibrosis, and kidney fibrosis. In still other embodiments of the above aspects, the inflammation is associated with a tissue selected from the group consisting of pulmonary, liver, brain or kidney tissue. In still other embodiments of the above aspects, the inflammation and/or fibrosis is associated with a condition selected from the group consisting of arthritis, arthrosclerosis, scleroderma, sarcoidosis, psoriasis, inflammatory eye diseases, ischemic and inflammatory cardiovascular diseases, and ischemic and inflammatory bowel diseases.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

When the terms "one," "a," or "an" are used in this disclosure, they mean "at least one" or "one or more," unless otherwise indicated.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "antibody" is meant any immunoglobulin polypeptide, or fragment thereof, having immunogen binding ability. As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains. In certain preferred embodiments, humanized antibodies may retain non-human residues within the human variable region framework domains to enhance proper binding characteristics.

As used herein, "antagonist" is meant to refer to a compound that inhibits a naturally occurring biological activity.

By "binds" is meant having a physicochemical affinity for that molecule. Binding may be measured by any of the methods of the invention.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, a "cryptic epitope" within a collagen is meant to refer to a sequence that is not exposed for recognition within a native collagen, but is capable of being recognized by an agent that binds denatured collagen. Peptide sequences that are not solvent exposed or are only partially solvent exposed in the native structure are potential cryptic epitopes. The sequence of cryptic epitopes can be identified by determining the specificity of an antagonist. Candidate cryptic epitopes also can be identified, for example, by examining the three dimensional structure of a native triple helical collagen.

As used herein "native collagen" is meant to refer to a collagen molecule that is predominately in its triple helical form. Exemplary collagens include but are not limited to collagen types I-IV.

As used herein "denatured collagen" is meant to refer to a collagen that is no longer predominantly in its native triple helical form. The denatured collagen can be denatured full-length collagen or a fragment of collagen. A fragment of collagen can be any collagen sequence shorter than a full length collagen sequence. The term "denatured collagen" encompasses "proteolyzed collagen". "Proteolyzed collagen" refers to a collagen that has been structurally altered through the action of a proteolytic enzyme.

"Detect" refers to identifying the presence, absence or amount of the object to be detected.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, an "epitope" is meant to refer to a region of a protein to which an antibody can bind. An epitope can be a linear peptide sequence or can be composed of non-contiguous amino acid sequences. An antagonist can recognize one or more sequences; therefore, an epitope can define more than one distinct amino acid sequence target. The epitopes recognized by an antagonist can be determined by peptide mapping and sequence analysis techniques well known to one of skill in the art.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 3, 5, 10, 20, 30, 40, 50, 60, 70, 80, 90, or 100, 200, 300, 400, 500, 600, 700, 800, 900, or 1000 nucleotides or amino acids.

The term "peptide" as used herein is meant to refer to a series of two or more covalently linked amino acids. A linear, cyclic, or branched peptide can be used in practicing the invention.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, "obtaining" as in "obtaining an agent" includes synthesizing, purchasing, or otherwise acquiring the agent.

By "proliferative disease" is meant a disease that is caused by or results in inappropriately high levels of cell division, inappropriately low levels of apoptosis, or both. For example, cancer is an example of a proliferative disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, rodent, or feline.

The terms "treat" and "treatment" are meant to refer to therapeutic or prophylactic interventions that favorably alter a pathological state. Treatments include procedures that moderate or reverse the progression of, reduce the severity of, prevent, or cure a disease. In addition, "treat", "treating", and "treatment" can also mean prolonging survival as compared to expected survival if not receiving treatment.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A-FIG. 1C show that the Clk-peptide reduced inflammation. FIG. 1A (Top left) shows that untreated CAM tissues exhibited minimal if any tissue thickening surrounding the central filter disc. In contrast, bFGF (FGF-2) potently induced a strong inflammatory response (Top right) as indicated by the robust thickening of CAM, which begins to overlap and partially cover the central area of the filter disc (Arrows). Similar results were noted under control peptide treated conditions (Bottom left) Importantly, treatment with CLK-peptide (250 ug/day) dramatically reduced the overall levels of inflammation (Bottom right) as compared to either bFGF-2 alone (Top right) or control peptide (Bottom left). To further examine the CM tissues, frozen sections of similar treated CAM tissues were stained by H&E (FIG. 1B). As shown in FIG. 1B (Top left), few eosinophillic infiltrates were observed in the untreated CAM tissues (Arrow). In contrast, FGF-2 potently induced a strong inflammatory response (Top right) as indicated by the robust infiltration of the eosinophillic (Pink) infiltrates (Arrows) Importantly, treatment with CLK-peptide dramatically reduced the overall levels of inflammatory infiltrates (Bottom left) as compared to either bFGF-2 alone (Top right) or control peptide (Bottom right). FIGS. 1C and 1D are graphs that quantify the effect of the CLK-peptide on inflammation.

DETAILED DESCRIPTION OF THE INVENTION

Figure 1A:
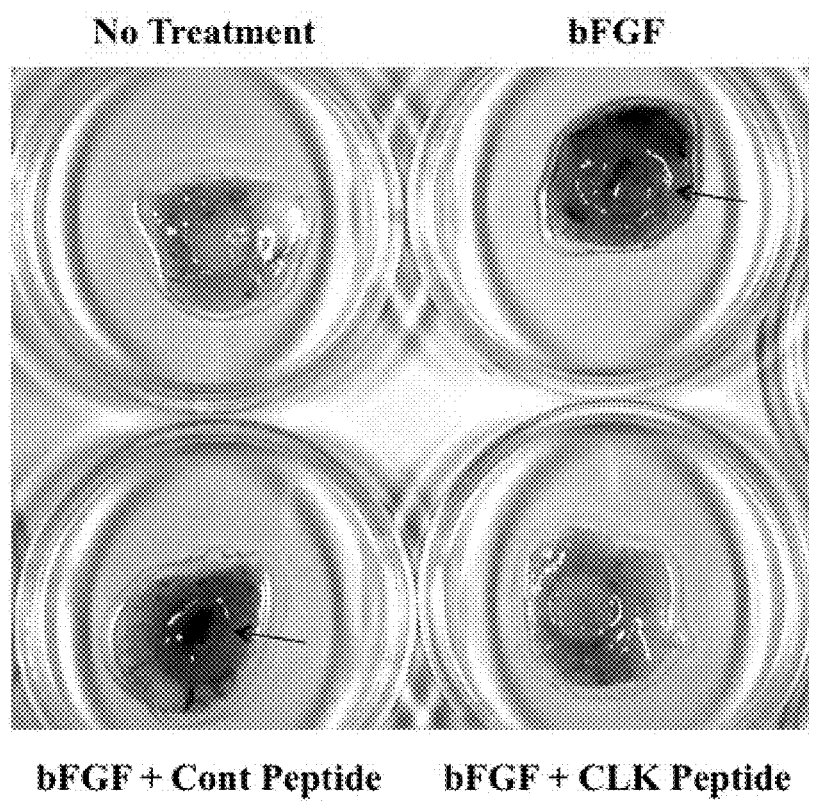

The invention provide compositions and methods for the prevention or treatment of inflammation and fibrosis using agents that inhibit binding to a non-cellular cryptic collagen epitope.

The invention is based, at least in part, on the discovery that agents that inhibit binding to a non-cellular cryptic collagen epitope physically and selectively prevent or reduce infiltration of many of the diverse cell types known to contribute to inflammation and fibrosis. In particular, as reported in more detail below, a peptide that targeted a cryptic collagen epitope inhibited infiltration of inflammatory cells in vivo. In addition, the CLK-peptide inhibited normal macrophage and fibroblast adhesion to denatured collagen. Accordingly, the invention provides agents that disrupt binding to a non-cellular cryptic collagen epitope recognized by the CLK-peptide, and the use of such agents for the treatment and/or prevention of conditions associated with inflammation and fibrosis. Advantageously, agents that bind to the cryptic collagen epitope simultaneously inhibit infiltration and localization of a variety of different cell types, each of which may produce and secrete many known pro-inflammatory molecules, rather than inhibiting the functional activity of one specific factor. Compositions and methods of the invention have significant therapeutic benefits over conventional anti-inflammatories, because the present compositions and methods limit local tissue access to numerous cell types and molecules required for fibrosis and inflammation. In addition, compositions and methods of the invention are unlikely to produce the adverse effects associated with many conventional anti-inflammatories because they target a highly selective epitope that is restricted to sites of tissue damage rather than a target that is broadly distributed, thus likely reducing the possibility of side effects. The compositions of the invention are particularly useful in treating a variety of diseases and disorders associated with angiogenesis and fibrosis, by potentially simultaneously inhibiting infiltration and localization of a variety of different cell types, each of which may produce and secrete many known pro-inflammatory molecules.

Collagen

Collagen is an extracellular matrix protein containing a [Gly-Xaa-Xaal]$_n$ sequence motif. Collagen is a fibrous multi-chain triple helical protein that exists in numerous forms. At least 18 genetically distinct types of collagen have been identified, many of which have distinct tissue distributions and functions. The mature collagen molecule is composed of two al chains and one α2 chain twisted into a triple helix. Collagens type-I and type-IV, for example, are composed of major chains designated α1(I) and α2 (I) and α1(IV) and α2(IV), respectively. In vivo, collagen is normally found in the mature triple helical form. Generally, a collagen is an extracellular matrix protein containing a [Gly-Xaa-Xaa]$_n$ sequence. Collagen types are well known in the art (see, e.g., Olsen, B. R. (1995) Curr. Op. Cell. Biol. 5:720-727; Kucharz, E. J. The Collagens: Biochemistry and Pathophysiology. Springer-Verlag, Berlin, 1992; Kunn, K. in Structure and Function of Collagen Types, eds: R. Mayne and R. E. Burgeson, Academic Press, Orlando). Human collagens are preferred collagens.

Denatured collagen refers to collagen that no longer predominantly assumes the native triple helical form. Denaturation of a collagen can be monitored, for example, by spectroscopic changes in optical properties such as absorbance, circular dichroism or fluorescence of the protein, by nuclear magnetic resonance, by Raman spectroscopy, or by any other suitable technique. Denatured collagen refers to denatured full length collagen, as well as to fragments of collagen. A fragment of collagen can be any collagen sequence shorter than a native collagen sequence. For fragments of collagen with substantial native structure, denaturation can be effected as for a native full-length collagen.

Fragments also can be of a size such that they do not possess significant native structure or possess regions without significant native structure of the native triple helical form. Such fragments are denatured all or in part without requiring the use of heat or of a chaotropic agent. The term denatured collagen encompasses proteolyzed collagen. Proteolyzed collagen refers to a collagen that has been fragmented through the action of a proteolytic enzyme. In particular, proteolyzed collagen can be prepared by treating the collagen with a metalloproteinase, such as MMP-1, MMP-2 or MMP-9, or by treating the collagen with a cellular extract containing collagen degrading activity.

Denatured Collagen

In vivo, changes in the structure of collagen are associated with UV-damage and other insults. As reported in more detail below, denatured collagen and/or fragments thereof likely facilitate inflammatory cell infiltration of sites of cellular damage. Agents that physically and/or selectively bind to denatured collage, particularly a cryptic epitope of collagen type I-IV, thereby blocking the binding of inflammatory cells, are useful for inhibiting inflammatory cell infiltration. Such agents are termed "antagonists" of denatured collagen. As used herein, a "cryptic epitope" within a collagen refers to a sequence that is not exposed for recognition within a native collagen, but that is capable of being recognized by an antagonist of a denatured collagen. Such antagonists physically and selectively bind to the denatured collagen and reduce or block the biological function of the denatured collagen. In particular, an agent that physically or selectively binds to a cryptic epitope within collagen reduces cell (e.g., fibroblast, macrophage) binding to the denatured collagen. Peptide sequences that are not solvent exposed or are only partially solvent exposed in the native structure are potential cryptic epitopes. The sequence of cryptic epitopes can be identified by determining the specificity of an antagonist. Candidate cryptic epitopes also can be identified, for example, by examining the three dimensional structure of a native triple helical collagen.

An epitope is an amino acid sequence or sequences that is recognized by an agent of the invention (e.g., an antibody). An epitope can be a linear peptide sequence or can be composed of noncontiguous amino acid sequences. An agent can recognize one or more sequences, therefore an epitope can define more than one distinct amino acid sequence target. An epitope recognized by an agent of the invention can be determined by peptide mapping and sequence analysis techniques well known to one of skill in the art.

In one embodiment, an agent of the invention selectively binds to a denatured collagen. The agent may bind to native collagen, but the agent binds with substantially reduced affinity to the native form of the collagen. A "substantially reduced affinity" is an affinity of about 3-fold lower than that for the denatured collagen, more preferably about 5-fold lower, and even more preferably about 10-fold lower, and even more preferably greater than 10-fold lower. Likewise, "substantially less" indicates a difference of at least about a 3-fold difference when referring to relative affinities. Antagonists may be specific for any one of the denatured collagens. In one embodiment, an agent of the invention binds specifically to denatured collagen type I-IV.

In another embodiment, the agent is a protein, peptide, antibody, aptamer, oligopeptide or small molecule inhibitor, or a fragment of one of these. In one preferred embodiment, the agent is an antibody. In another embodiment, the agent is the CLK/HUI77 cryptic epitope OGAKGLPGPOG-POGPY (SEQ ID NO: 1).

In certain preferred embodiments, the agent reduces the infiltration of one or more types of inflammatory cells. In other preferred embodiments, the agent reduces macrophage adhesion or reduces fibroblast cell adhesion to denatured collagen type-IV. Methods for assaying adhesion are described in the Examples. In still other embodiments, cell adhesion is measured using radioactivity, staining methods (e.g., staining cells with a dye, such as crystal violet), or with a fluorescent probe. US Application No. 20040242490, incorporated by reference in its entirety herein, describes denatured collagen type-IV selective antagonists.

In one embodiment, an agent of the present invention has the amino acid core sequence L-K-Q-N-G-G-N-F-S-L (SEQ ID NO: 4). One preferred agent for use in the present invention is the CLK-peptide. A CLK-peptide binds to denatured collagen type-IV with high specificity. The amino acid sequence of CLK peptide is C-L-K-Q-N-G-G-N-F-S-L-G (SEQ ID NO: 6). The CLK-peptide binds to regions within denatured collagen type-IV and inhibits cellular interactions with denatured collagen type-IV.

Another preferred selective denatured collagen type-IV antagonist for use in the present invention is SLK-peptide. SLK-peptide binds with high specificity to denatured collagen type-IV and inhibits cellular interactions with denatured collagen type-IV. The amino acid sequence of SLK-peptide is S-L-K-Q-N-G-G-N-F-S-L-C(SEQ ID NO: 7).

A further preferred selective denatured collagen type-IV antagonist for use in the present invention is KGGCLK peptide ("KGGCLK" disclosed as SEQ ID NO: 10). KGGCLK peptide ("KGGCLK" disclosed as SEQ ID NO: 10) binds with high specificity to denatured collagen type-IV and inhibits cellular interactions with denatured collagen type-IV. The amino acid sequence of KGGCLK peptide ("KGGCLK" disclosed as SEQ ID NO: 10) is -K-G-G-C-L-K-Q-N-G-G-N-F-S-L-G-G-K (SEQ ID NO: 8).

Agents that bind to denatured collagen can be identified using any method known in the art. In one embodiment, sequential solid phase binding assays, for example, are used to identify denatured collagen type-IV selective antagonists. Preferred methods for identifying denatured collagen type-IV antagonists are subtractive immunization (Xu, J. et al. (2000) Hybridoma, Vol. 19:375-385) and subtractive phage display (Amstutz P., et al. (2001) Curr. Opin. Biotechnol., vol. 12:400-405).

Denatured collagen is produced using any method known in the art. A preferred method of denaturation is thermal denaturation because thermal denaturation results in fewer small fragments that may have little immunogenicity in vivo. Collagen type-IV can be thermally denatured by, for example, heating collagen type-IV to 100° C. for fifteen minutes. Denaturation can also be accomplished by treating the collagen with a chaotropic agent. Suitable chaotropic agents include, for example, guanidinium salts. Collagen can also be denatured by ionizing radiation, non-ionizing radiation (ultraviolet), thermal injury, and mechanical stress or force. Collagen can be denatured by proteolysis. In particular, proteolyzed collagen can be prepared by treating the collagen with a metalloproteinase, such as MMP-1, MMP-2 or MMP-9, or by treating the collagen with a cellular extract containing collagen degrading activity. Proteolyzed collagen may also occur naturally at sites of neovascularization, tumor growth, metastasis, bacterial invasion, arthritis and inflammation in a tissue.

Denaturation of a collagen can be monitored, for example, by spectroscopic changes in optical properties such as absorbance, circular dichroism or fluorescence of the protein, by nuclear magnetic resonance, by Raman spectroscopy, or by any other suitable technique.

The resultant denatured collagen type-IV fragments can then be fixed to a solid matrix. Peptides known to bind collagen can be obtained from a peptide library. (Amstutz P., et al. (2001) Curr. Opin. Biotechnol., vol. 12:400-405). The collagen-binding peptides can be passed over the solid matrix. Peptides that bind denatured collagen type-IV adhere to the solid matrix. The adherent peptides can then be washed from the solid matrix and then passed over a second solid matrix to which native collagen type-IV is fixed. Peptides that do not bind to the second solid matrix are denatured collagen type-IV selective antagonists.

Agents that selectively bind to denatured collagen can be generated using several different techniques that are well known to those skilled in the art. In one embodiment, a two hybrid system (e.g., Fields, S. (1989) Nature 340:245-6) uses a collagen fragment as "bait" for selecting protein antagonists from a library that binds to the collagen peptide. This system and its operation are described in Green, D. M., et al., Proc. Natl. Acad. Sci. USA. 100:1010-1015 (2003) and in Gyuris, J. et al. (1993) Cell, Vol. 75: 791-803. The library of potential antagonists can be derived from a cDNA library, for example. In another embodiment, the potential antagonists can be variants of known collagen binding proteins, such as integrins and fibronectin. (Hynes, R. O. (1992) Cell, Vol. 69:11-25; Steffensen, B., et al. (2002) Matrix Biol., Vol. 21:399-414; Ingham, K. C., et al. (2002) Arch. Biochem. Biophys., Vol. 407:217-223). Such proteins can be randomly mutagenized or subjected to gene shuffling, or other well known techniques for generating sequence diversity (Tani, P. H., et al. (2002) Biochm. J., Vol. 365: 287-294; Stephanopoulos, G. (2002) Nat. Biotechnol., Vol. 20:666-668).

Peptide antagonists of the invention also can be generated using molecular evolution techniques as disclosed in Zhao, H., et al. (2002) Cur. Opin. Biotechnol., Vol. 13:104-110 and Guo, Z., et al. (2002) Biochemistry, Vol. 41:10603-10607. Libraries of proteins can be generated by mutagenesis, gene shuffling or other well known techniques for generating molecular diversity. Protein pools representing numerous variants can be selected for their ability to bind to denatured collagen, for instance, by passing such protein pools over a solid matrix to which a denatured collagen has been attached. Elution with gradients of salt, for example, can provide purification of variants with affinity for the denatured collagen. A negative selection step also can be included whereby such pools are passed over a solid matrix to which native collagens have been attached. The filtrate will contain those variants with in the pool that have a reduced affinity for the native form of the collagen.

The peptide and polypeptide antagonists of the present invention also can be generated by phage display. Phage display is a selection technique in which a peptide is expressed as a fusion with a coat protein of a bacteriophage. The result is that the fused protein is displayed on the surface of the viron and the DNA encoding the fusion protein resides within the viron. (Smith G. P. (1985) Filamentous fusion phage: Novel expression vectors that display cloned antigens on the viron surface. Science. 228:1315-1317; Smith G. P., et al. (1993) Libraries of peptides and proteins displayed on filamentous phage. Methods Enzymol. 217: 228-257). Phage display allows for rapid identification of peptide ligands for a variety of target molecules using an in vitro process called panning. Panning is carried out, for example, by incubating a library of phage-displayed peptides with a microtiter plate coated with the target, washing away the unbound phage, and eluting the bound phage. The eluted phage is then amplified and taken through additional binding/amplification cycles to enrich the pool in favor of binding sequences. After 3-4 rounds of panning, individual clones are identified by DNA sequencing.

A randomized peptide or protein can be expressed on the surface of a phagemid (a term for the combination of phage and plasmid) particle as a fusion with a phage coat protein. Techniques of monovalent phage display are widely available (see, e.g., Lowman H. B. et al. (1991) Biochemistry 30:10832-8). Phage expressing randomized peptide or protein libraries can be panned with a solid matrix to which a native collagen molecule has been attached. Remaining phage do not bind native collagens, or bind native collagens with substantially reduced affinity. The phage are then panned against a solid matrix to which a denatured collagen has been attached. Bound phage are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

The well known ELISA assay can be used to identify collagen type-IV selective antagonists for use in practicing the present invention. A peptide or polypeptide can be identified as an antagonist through the use of a solid phase ELISA to determine whether the peptide or polypeptide binds to denatured or native collagens. The ELISA assay is useful with a variety of collagen types; for example, the ELISA assay can be used with collagens types I, II, III, IV, and V, as well as for other extracellular matrix components. The level of binding affinity can be determined by surface plasmon resonance technique (analyzed on a BIOCORE 2000 system) (Liljeblad, et al. (2000) Glyco. J., vol. 17:323-329) and standard measurements by traditional scatchard binding assays (Heeley, R. P. (2002) Endocr. Res., Vol. 28:217-229).

Solid phase ELISA also can be used to identify compounds which exhibit specificity for denatured, but not native, forms of collagen. The specificity assay is conducted by running parallel ELISAs where a potential antagonist is screened concurrently in separate assay chambers for the ability to bind denatured and native collagens.

Antagonists of the invention can also be identified by their ability to bind to a solid matrix containing a denatured collagen. Putative antagonists are collected after altering solution conditions, such as salt concentration, pH, temperature, or other conditions. The putative antagonists are further identified by their ability to pass through, under appropriate solution conditions, a solid matrix to which a native collagen has been affixed.

Agents of the present invention can be used with collagen type I-IV molecules from any invertebrate or vertebrate animal, including humans. Examples of collagen type I-IV molecules are found in Engel, J. (1997) Science, Vol. 277:1785-1786 and Gordon, M. K., et al., (1990) Curr. Opin. Cell Biol., Vol. 2:833-838. Preferably, the collagen type-IV is a mammalian collagen type-IV. More preferably, the mammal is a pig, cow, goat, rabbit, mouse, rat, dog, cat, sheep, donkey, horse, or mule. In one particular embodiment, the collagen is human collagen type-IV.

Active agents for use in the invention comprise one or more denatured collagen type-IV antagonists. An antagonist of denatured collagen type I-IV can be any peptide, polypeptide or peptido-mimetic that has substantially greater binding affinity to denatured collagen type I-IV than to the native form of collagen type I-IV and that blocks denatured collagen type I-IV biological activity (e.g., cell adhesion). The peptide antagonists of the present invention may be modified, for example, by phosphorylation, hydroxylation or methylation. Additional modifications that may enhance activity include peptide cyclization and peptide stabilization.

Peptide Antagonists of Denatured Collagen and Analogs

Also included in the invention are peptide antagonist of any denatured collagen, including but not limited to types I-IV or fragments thereof that are modified in ways that enhance or do not inhibit their ability to modulate an inflammatory cell response. In one embodiment, the invention provides methods for optimizing an amino acid sequence or nucleic acid sequence by producing an alteration. Such changes may include certain mutations, deletions, insertions, or post-translational modifications.

In one embodiment, the present invention includes analogs, fragments, or chemical derivatives of a polypeptide whose amino acid residue sequence delineated herein so long as the peptide is a selective antagonist of denatured collagen type I-IV. Therefore, a peptide can be subject to various changes, substitutions, insertions, and deletions where such changes provide for certain advantages in its use. In this regard, a denatured collagen type I-IV antagonist peptide of this invention includes the sequence of a recited peptide where one or more sequence changes are made and the peptide retains the ability to function as a denatured collagen type I-IV selective antagonist in one or more of the assays as defined herein.

The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues. Again, in an exemplary approach to determining the degree of identity, a BLAST program may be used, with a *probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes fragments of any one of the polypeptides of the invention. As used herein, the term "a fragment" means at least 2, 3, 4, 5, 10, 13, or 15 amino acids. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein antagonists of denatured collagen type I-IV analogs having a chemical structure designed to mimic antagonists functional activity can be administered according to methods of the invention. Antagonist of denatured collagen type I-IV analogs may exceed the physiological activity of the CLK peptide. Methods of analog design are well known in the art, and synthesis of analogs can be carried out according to such methods by modifying the chemical structures such that the resultant analogs exhibit the modulatory activity of the CLK peptide. These chemical modifications include, but are not limited to, substituting alternative R groups and varying the degree of saturation at specific carbon atoms of the CLK peptide. Preferably, the CLK peptide analogs are relatively resistant to in vivo degradation, resulting in a more prolonged therapeutic effect upon administration. Assays for measuring functional activity include, but are not limited to, those described in the Examples below.

KGGCLK-peptide ("KGGCLK" disclosed as SEQ ID NO: 10) is one such modified peptide, KGGCLK-peptide ("KGGCLK" disclosed as SEQ ID NO: 10) is CLK-peptide with sequence KGG added to the N-terminus and GKA added to the C-terminus. The coupling of the amino acids may be accomplished by techniques familiar to those in the art and provided, for example, in Stewart and Young, 1984, Solid Phase Synthesis, Second Edition, Pierce Chemical Co., Rockford, Ill.

The antagonist can be conjugated with therapeutic agents or cytotoxins for delivery to a site of inflammation or to fibrotic tissue, or other disease or condition associated with cellular interactions with denatured collagen type-IV. Such conjugates can be made with a cytolysin or an exotoxin, for example ricin A, diphtheria toxin A, or Pseudomonas exotoxin and fragments thereof. The cytotoxic agent can also be a radioactively labeled with an isotope so as to locally deliver a toxic dose of radioactivity to a tissue undergoing cellular interaction with denatured collagen type-IV.

Denatured Collagen Binding Assays

The invention also provides assay methods for identifying agents that bind to denatured collagen for use in reducing inflammation, fibrosis, UV radiation damage, or any other method delineated herein. In these assays, agents are evaluated for their ability to bind both denatured collagen and native collagen, and furthermore can be evaluated for their efficacy in reducing the binding of one or more types of inflammatory cells to denatured collagen.

A first assay measures binding of agents to denatured or native collagens in the solid phase by ELISA. The assay is useful with a variety of types of collagens, for example, the assay can be used with collagens types I, II, III, IV and V, as well as for other extracellular matrix components.

The assay also can be used to identify compounds which exhibit specificity for denatured but not native forms of collagen. The specificity assay is conducted by running parallel ELISAs where a potential antagonist is screened concurrently in separate assay chambers for the ability to bind denatured and native collagens.

Antagonists of denatured collagen can also be identified by their ability to compete for binding with a known denatured collagen antagonist. For example, antagonists can be identified by monitoring their effect on the affinity of binding to denatured collagen of a known antagonist, such as HUI77 or D93, or in a binding assay, such as ELISA. Such antagonists likely have the same specificity as HUI77, and recognize the same cryptic epitope. Antagonists can be selected from the putative antagonists by conventional binding assays to determine those that bind to the denatured collagen epitope but not to the known antagonist.

Antagonists can also be identified by their ability to bind to a solid matrix containing a denatured collagen. Such putative antagonists are collected after altering solution conditions, such as salt concentration, pH, temperature, and other conditions. The putative antagonists are further identified by their ability to pass through, under appropriate solution conditions, a solid matrix to which a native collagen has been affixed.

Non-Peptide Agents

The invention also provides small organic molecules, such as those natural products, or those compounds synthesized by conventional organic synthesis or combinatorial organic synthesis that selectively bind to denatured collagen and thereby inhibit the binding of an inflammatory cell. Compounds can be tested for their ability to bind to a denatured collagen, for example, by using the column binding technique described above. Compounds also are selected for reduced affinity for the native form of the collagen by a similar column binding technique.

Other suitable non-peptidic compounds include, for example, oligonucleotides. Oligonucleotides as used herein refers to any heteropolymeric material containing purine, pyrimidine and other aromatic bases. DNA and RNA oligonucleotides are suitable for use with the invention, as are oligonucleotides with sugar (e.g., 2' alkylated riboses) and backbone modifications (e.g., phosphorothioate oligonucleotides). Oligonucleotides may present commonly found purine and pyrimidine bases such as adenine, thymine, guanine, cytidine and uridine, as well as bases modified within the heterocyclic ring portion (e.g., 7-deazaguanine) or in exocyclic positions. Oligonucleotide also encompasses heteropolymers with distinct structures that also present aromatic bases, including polyamide nucleic acids and the like.

An oligonucleotide antagonist of the invention can be generated by a number of methods known to one of skill in the art. In one embodiment, a pool of oligonucleotides is generated containing a large number of sequences. Pools can be generated, for example, by solid phase synthesis using mixtures of monomers at an elongation step. The pool of oligonucleotides is sorted by passing a solution-containing the pool over a solid matrix to which a denatured collagen or fragment thereof has been affixed. Sequences within the pool that bind to the denatured collagen are retained on the solid matrix. These sequences are eluted with a solution of different salt concentration or pH. Sequences selected are subjected to a second selection step. The selected pool is passed over a second solid matrix to which native collagen has been affixed. The column retains those sequences that bind to the native collagen, thus, enriching the pool for sequences specific for the denatured collagen. The pool can be amplified and, if necessary, mutagenized and the process repeated until the pool shows the characterstics of an antagonist of the invention. Individual antagonists can be identified by sequencing members of the oligonucleotide pool, usually after cloning said sequences into a host organism such as *E. coli*.

Antibodies

In certain preferred embodiments, the present invention provides denatured collagen antagonists in the form of antibodies. Antibody antagonists as described by the present invention can be used to alter the activity of one or more types of inflammatory cells in a subject. Antibody antagonists as described by the present invention can be used to treat or prevent fibrosis or inflammation.

Antibodies are well known to those of ordinary skill in the science of immunology. As used herein, the term "antibodies" includes polyclonal antibodies, affinity-purified polyclonal antibodies, monoclonal antibodies, and antigen-binding fragments, such as F(ab')2 and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains. In certain preferred embodiments, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

"Antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983).

Examples of antibodies include monoclonal antibodies, polyclonal antibodies, the preparation and use of which are known to the skilled artisan. Other exemplary antibodies include whole native antibodies, bispecific antibodies, Fab, Fab', single chain V region fragments (scFv) and fusion polypeptides. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

The phrase "monoclonal antibody" refers to a population of antibody molecules that contain only one species of antibody combining site capable of immunoreacting with a particular epitope. A monoclonal antibody may therefore contain an antibody molecule having a plurality of antibody combining sites, each immunospecific for a different epitope, e.g., a bispecific monoclonal antibody.

In certain preferred embodiments, monoclonal antibodies which preferentially bind to denatured collagen include monoclonal antibodies having the immunoreaction characteristics of mAb HUI77, mAb D93, mAb HUIV26 or mAb XL313.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')₂," fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art, where the target is denatured collagen, preferably denatured collagen type-IV, and in particular, wherein the target is a cryptic collagen epitope as described herein (e.g., the CLK/HU177 or CLK/D93 cryptic epitope), or immunogenic fragments thereof, as an immunogen.

An "epitope" is a region of a protein to which an antibody can bind. See, for example, Geysen et al., Proc. Natl. Acad. Sci. USA 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., Science 219:660-666, 1983 Immunogenic, epitope-bearing polypeptides contain a sequence of at least six, often at least nine, more often from 15 to about 30 contiguous amino acid residues of denatured collagen (e.g., collagen type I-IV).

In certain embodiments, an agent of the invention specifically binds to an epitope of denatured collagen (e.g., collagen type I-IV). In particular embodiments, the epitope comprises at least a core GLPGP (SEQ ID NO: 11) amino acid sequence. Such sequences are present in may different types of collagen (e.g., collagen type I-IV).

In certain preferred examples, the epitope corresponds to OGAKGLPGPOGPOGPY, SEQ ID NO: 1, where O represents hydroxylated prolines. Polypeptides comprising a larger portion of a denatured collagen (e.g., collagen type I-IV), i.e., from 30 to 50 residues, up to the entire sequence are included.

One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a cryptic collagen epitope as described herein (e.g., the CLK/HU177 or CLK/D93 cryptic epitope), or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a cryptic collagen epitope as described herein (e.g., the CLK/HU177 or CLK/D93 cryptic epitope), or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column, preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition, e.g., Pristane.

Monoclonal antibodies (Mabs) can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In particular embodiments of the invention, an antibody is used to detect a non-cellular cryptic collagen epitope. The antibody can be prepared against any non-cellular cryptic collagen epitope using techniques discussed and known to one of ordinary skill in the art. In one example, to detect a collagen cryptic epitope, the antibody can be prepared against the sequence OGAKGLPGPOGPOGPY, SEQ ID NO: 1).

In certain cases, the immunogenicity of a polypeptide immunogen may be increased through the use of an adjuvant.

Alternative techniques for generating or selecting antibodies include in vitro exposure of lymphocytes to a polypeptide immunogen, and selection of antibody display libraries in phage or similar vectors (for instance, through use of immobilized or labeled polypeptide). Techniques for creating and screening such random peptide display libraries are known in the art (e.g., Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the epitope sequences disclosed herein to identify proteins that bind to preferred epitopes.

Antibodies are determined to be specifically binding if they bind to their intended target (e.g., denatured collagen types I, II, III, IV) with a greater affinity than the binding affinity to control (e.g., non-denatured collagen type-IV) polypeptide or protein. The binding affinity of an antibody can be readily determined by one of ordinary skill in the art, for example, by Scatchard analysis (Scatchard, G., Ann. NY Acad. Sci. 51: 660-672, 1949). Methods for screening and isolating specific antibodies are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; and Benjamin et al., Ann. Rev. Immunol. 2:67-101, 1984.

A variety of assays known to those skilled in the art can be utilized to detect antibodies that specifically bind to denatured collagen (e.g., denatured collagen types I, II, III, IV). Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

Methods of Treatment

The present invention describes a novel method to prevent and/or inhibit inflammation and fibrosis by targeting denatured collagen, and in particular denatured collagen type-IV, with antagonists. The methods of the present invention selectively prevent or reduce infiltration of the many of the diverse cell types known to contribute to inflammation and fibrosis, rather than inhibiting the action of one individual molecule, and so represent a much more efficacious clinical approach to treat inflammation and fibrosis.

The invention provides methods for treating or preventing fibrosis or inflammation in a subject comprising administering to the subject a composition comprising a therapeutically effective amount of an agent (e.g., proteins, peptides, antibodies, aptamers, oligopeptides and small molecule inhibitors) that selectively binds denatured collagen (e.g., denatured collagen types I, II, III, IV).

In other aspect, the methods of the invention can be used to treat cancer. Accordingly, the invention features methods of treating or preventing the development or spread of cancer in a subject comprising administering to the subject a composition comprising a therapeutically effective amount of an agent that binds denatured collagen (e.g., denatured collagen types I, II, III, IV). Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In certain preferred examples, the cancer is melanoma. In other preferred examples, the antagonist is administered prior to the onset of the cancer.

Fibroproliferative Diseases

Fibroproliferative disorders are characterized by the abnormal accumulation of fibrous tissue ("fibrosis") that can occur as a part of the wound-healing process in damaged tissue. Such tissue damage may result from physical injury, inflammation, infection, exposure to toxins, and/or other causes. The fibroproliferative condition includes both a cell growth component and an extensive phase characterized by extracellular matrix accumulation. Fibroproliferative diseases, include, for example, excessive skin scarring, keloid formation, myocardial scarring, vascular restenosis, intestinal stricture formation, thoracic and abdominal postsurgical adhesion formation, articular, pannus formation, pulmonary fibroses, systemic sclerosis, liver cirrhosis, cardiovascular disease, progressive kidney disease, and macular degeneration, and can affect all tissues and organ systems. Further, fibrotic tissue remodeling can also influence cancer metastasis and accelerate chronic graft rejection in transplant recipients.

Pathogenic fibrosis is often associated with a chronic inflammatory reaction. A chronic inflammatory reaction is one that lasts for several weeks (e.g., 2, 3, 4, 5, or 6 weeks) or months (e.g., 2, 3, 4, 5, 6, 8, 9, 10, 11, 12 months or longer) and generally includes inflammation, tissue destruction, and/or repair processes. In general, chronic fibrotic disorders have in common a persistent irritant that sustains the production of growth factors, proteolytic enzymes, angiogenic factors, and fibrogenic cytokines, which together stimulate the deposition of connective tissue elements that progressively remodel and destroy normal tissue architecture (Tomasek J. J et al. Nat. Rev. Mol. Cell Biol. 2002; Friedman S. L., Nat. Clin. Pract. Gastroenterol. Hepatol. 2004).

Pulmonary fibrosis is a major cause of morbidity and mortality. In one embodiment, pulmonary fibrosis is associated with the use of high-dose antineoplastic agents (e.g., bleomycin) in chemotherapy and with bone marrow transplantation for cancer treatment. The development of lung disease is the major dose-limiting side effect of bleomycin. See, Tran et al., J. Clin. Invest. 99:608-617, 1997. Idiopathic pulmonary fibrosis (IPF) is another lung fibrotic disease characterized by a fibroproliferative response. Various factors, including aspiration and exposure to environmental pollutants may result in IPF (Egan, The Lancet 354:1839-1840, 1999). The standard treatment for IPF is oral glucocorticoids. However, lung function improves in less than 30 percent of patients who receive this treatment, and, regardless of treatment, the median survival is four to five years after the onset of symptoms. The proliferation of fibroblasts and the accumulation of interstitial collagens are the hallmarks of progressive organ fibrosis; however, the biochemical mechanism of induction of lung fibrosis remains unclear (Ziesche et al., New Eng. J. Med. 341:1264-1269, 1999; Kuwano et al., J. Clin Invest. 104:13-19, 1999). Pulmonary hypertension results from a variety of initiating stimuli. Its progression is associated with pulmonary vascular sclerosis, which includes abnormal endothelial morphology and function, muscularization of normally nonmuscular peripheral arteries related to differentiation of pericytes, and medial hypertrophy and neointimal formation in muscular arteries as a consequence of hypertrophy, proliferation, and migration of resident smooth muscle cells and increased production of extracellular matrix components. These components include collagen, elastin, fibronectin, and tenascin-C. This fibroproliferative response can progress to life-threatening pulmonary arterial obstructive disease (Cowan et al., J. Clin. Invest. 105:21-34, 2000).

Fibroproliferative disorders of the lung include, but are not limited to, for example, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C.

Effects of the antagonists of the present invention on lung fibrosis can also be assayed in a mouse model using bleomycin. The chemotherapy agent bleomycin is a known causative agent of pulmonary fibrosis in humans and can induce interstitial lung disease in mice, including an increase in the number of fibroblasts, enhanced collagen deposition, and dysregulated matrix remodeling. C57B1/6 mice are administered bleomycin by osmotic minipump for 1 week. There follows a period of inflammation, with cutaneous toxicity beginning approximately 4-7 days after bleomycin administration and continuing for about a week, after which the mice appear to regain health. About 3-4 weeks after the finish of bleomycin delivery, the mice are sacrificed, and the lungs are examined histologically for signs of fibrosis. Scoring is based on the extent of lung fibrotic lesions and their severity. Serum is assayed for lactic dehydrogenase, an intracellular enzyme that is released into the circulation upon general cell death or injury. Lung tissue is assayed for hydroxyproline as a measure of collagen deposition.

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a "classic" fibroproliferative disease. See, Miller et al., Circulation 101:1598-1605, 2000).

Liver fibrosis is the excessive accumulation of extracellular matrix proteins including collagen that occurs in most types of chronic liver diseases. Advanced liver fibrosis results in cirrhosis, liver failure, and portal hypertension and often requires liver transplantation.

A variety of renal diseases can be classified as fibroproliferative. Glomerular (usually mesangial) cell proliferation occurs in many types of glomerulonephritides in conjunction with increased extracellular matrix accumulation (Iida et al., Proc. Natl. Acad. Sci. USA 88:6560-6564, 1991). For example, mesangial cell proliferation precedes glomerulosclerosis in the remnant kidney model (Floege et al., Kidney International 41:297-309, 1992), and experimental overexpression of growth factors such as PDGF-B and TGF-beta in the kidney induces cell proliferation, matrix accumulation, and glomerulosclerosis (Isaka et al., J. Clin. Invest. 92:2597-2601, 1993; Cybulsky, Curr. Opin. Nephropathy and Hypert. 9:217-223, 2000).

Fibroproliferative disorders of the kidney include, but are not limited to, glomerulonephritis (including membranoproliferative, diffuse proliferative, rapidly progressive, and chronic forms), diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, and nephrotic syndrome. The glomerulus is a major target of many types of renal injury, including immunologic (e g, immune-complex- or T-cell-mediated), hemodynamic (systemic or renal hypertension), metabolic (e.g., diabetes), "atherosclerotic" (accumulation of lipids in the glomerulus), infiltrative (e.g., amyloid), and toxic (e.g., snake venom) injuries (Johnson, Kidney Int. 45:1769-1782, 1994). The renal structural changes in patients with diabetic nephropathy include hypertrophy of the glomerulus, thickening of the glomerular and tubular membranes (due to accumulated matrix), and increased amounts of matrix in the measangium and tubulointerstitium (Ziyadeh et al., Proc. Natl. Acad. Sci. USA 97:8015-8020, 2000). Glomerular hypertension due to intrarenal hemodynamic changes in diabetes can contribute to the progression of diabetic nephropathy (Ishida et al., Diabetes 48:595-602, 1999). Autoimmune nephritis can also lead to altered mesangial cell growth responses (Liu and Ooi, J. Immunol. 151:2247-2251, 1993). Infection by hepatitis-C virus can also result in idiopathic membranoproliferative glomerulonephritis (Johnson et al., N. Engl. J. Med. 328:465-470, 1993).

Effects of antagonists of the invention on liver and kidney fibrosis can be tested in known animal models, such as the db/db mouse model disclosed by Cohen et al., Diabetologia 39:270-274, 1996 and Cohen et al., J. Clin. Invest. 95:2338-2345, 1995, or transgenic animal models (Imai et al., Contrib. Nephrol. 107:205-215, 1994).

Inflammation Associated Diseases

Inflammation is the result of a complex series of molecular signals involving the immune system, usually in response to infection or cellular or tissue damage. Inflammation normally constitutes the body's initiation of healing; however, when it is not properly regulated inflammation can result in chronic diseases, such as arthritis.

By "inflammatory response" or "immune response" is meant the reaction of living tissues to injury, infection or irritation characterized by redness, warmth, swelling, pain, and loss of function produced, as the result of increased blood flow and an influx of immune cells and secretions. Inflammation is the body's reaction to invading infectious microorganisms and results in an increase in blood flow to the affected area, the release of chemicals that attract white blood cells, an increased flow of plasma, and the arrival of monocytes to clean up the debris. Anything that stimulates the inflammatory response is said to be inflammatory.

The innate cascade, or the innate immune response, is the non-specific response mounted by the immune system and is characterized by the infiltration of cells, such as leukocytes, natural killer cells, mast cells, eosinophils and basophils, as well as phagocytes, such as neutrophils, macrophages and dendritic cells in response to chemotatic signaling at the site of injury or infection. Molecules secreted by the aforementioned cells, such as histamine and various cytokines; and the complement system of circulating proteins contribute to inflammation. Diseases characterized by inflammation are significant causes of morbidity and mortality in humans. Commonly, inflammation occurs as a defensive response to invasion of the host by foreign, particularly microbial, material. Responses to mechanical trauma, toxins, and neoplasia also may results in inflammatory reactions.

In certain embodiments, the inflammatory disorder is a rheumatoid disorder. Rheumatoid disorders, as used herein, refer to any of a variety of inflammatory disorders characterized by inflammation, and sometimes degeneration and/or metabolic derangement, of the connective tissue structures, especially the joints, ligaments, and tendons. Rheumatoid disorders typically result in pain, stiffness, and/or limitation of motion. The particular tissue or tissues effected depends on the rheumatoid disorder. Exemplary rheumatoid disorders include, but are not limited to, rheumatoid arthritis, juvenile arthritis, bursitis, spondylitis, gout, scleroderma, Still's disease, and vasculitis.

In certain embodiments, the rheumatoid disorder is rheumatoid arthritis and "treating" rheumatoid arthritis includes decreasing the severity, frequency, and/or occurrence of one or more of the symptoms of rheumatoid arthritis. In other embodiments, the rheumatoid disorder is juvenile arthritis, bursitis, spondylitis, gout, scleroderma, Still's disease, or vasculitis. Methods of the invention decrease the severity, frequency, and/or occurrence of any one or more of the symptoms of these conditions.

In various embodiments, symptoms of arthritis or other inflammatory diseases include redness, swelling, inflammation, fever, decreased range of motion, and pain. Examples of reducing the occurrence or severity of symptoms include, but are not limited to, decreasing the number of swollen joints, decreasing the number of painful joints, decreasing the reliance on pain medication, decreasing a patient's self-evaluation of the frequency or severity of their pain, increasing freedom of motion, increasing mobility, decreasing fever, and increasing the ability to perform daily tasks.

Neuroinflammation, characterized by activated microglia and astrocytes and local expression of a wide range of inflammatory mediators, is a fundamental reaction to brain injury, whether by trauma, stroke, infection, or neurodegeneration. This local tissue response is thought to be part of a repair and restorative process. Like many inflammatory conditions in peripheral diseases, neuroinflammation can contribute to the pathophysiology of CNS disorders. For example, in Alzheimer's disease (AD), glial-driven inflammatory responses to AB deposition are thought to promote neurodegeneration, as evidenced by the extent of neuroinflammation in AD, increased risk for AD with certain polymorphisms of proinflammatory cytokine genes, and reduction in disease risk for individuals taking nonsteroidal anti-inflammatory drugs (NSAIDs).

In certain embodiment, the inflammatory disorder is an inflammatory skin disorder. Inflammatory skin disorders include but are not limited to rosacea, atopic dermatitis, acne, seborrheic dermatitis, and cellulitis.

In other embodiments, the inflammatory disease is an ischemic or inflammatory cardiovascular disease. An inflammatory cardiovascular disease or disorder may be, but is not limited to, an occlusive disease or disorder, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, or thrombosis. In other embodiments, the site is a secondary site of ischemic injury, such as the CNS or kidney.

In other embodiments, the inflammatory disease is an ischemic or inflammatory bowel disease.

Inflammatory bowel disease (IBD) refers to a chronic recurrent inflammatory disease of unclear etiology affecting the small intestine and colon that includes both Crohn's disease (CD) and ulcerative colitis (UC). Crohn's disease can involve any portion of the intestinal tract but most commonly involves the distal small intestine and/or the colon. Ulcerative colitis involves only the colon, generally limited to the rectum or distal colon. Studies of murine models of CD and UC strongly suggest that both of these diseases are due to dysregulation of the mucosal immune response to antigens in the mucosal microflora (Sartor, R. B. (1995). Gastroenterol Clin North Am 24, 475-507) (Strober W, et al. (2002) Annu. Rev. Immunol. 20:495-549).

Ulcerative colitis or indeterminate colitis refers to a condition of the colon characterized by a state of inflammation in which one or more of the following histological characteristics are detectable: a superficial inflammation characterized by the presence of epithelial cell loss and patchy ulceration, pronounced depletion of mucin producing-goblet cells, and reduction of the density of the tubular glands. In addition, in the lamina propia, a mixed inflammatory cell infiltrate consisting of lymphocytes and granulocytes (the latter consisting mostly of neutrophils and, to a lesser extent, eosinophils) associated with an exudation of cells into the bowel lumen is observed. Also, the submucosal level can display marked edema with few inflammatory cells, while in the outer muscle layer one of skill in the art would see little or no evidence of inflammation. See e.g. Boirivant et al. Journal of Experimental Medicine 188: 1929-1939 (1998). Clinical symptoms can include, but are not limited to, diarrhea, rectal prolapse, weight loss, abdominal pain, and dehydration.

Crohn's disease refers to inflammation affecting any part of the alimentary tract but most often affecting the terminal part of the small bowel and/or the adjacent ascending colon. Frequently, the inflammation is characterized by "skip lesions" consisting of areas of inflammation alternating with areas of normal mucosa. The affected area of bowel in Crohn's is marked by erythema, edema and increased friability; at times the bowel is strictured and attached to other abdominal organs or to the bowel wall. Fistulae between the affected bowel and other structures including the skin are not infrequent. Microscopic examination of the tissue in Crohn's disease reveals epithelial erosions, loss of mucin-producing goblet cells and an extensive lymphocytic infiltration involving all layers of the mucosa; this infiltrate sometimes contains giant cells indicative of granuloma formation. When inflammation is present for a long time (chronic), it sometimes can cause scarring (fibrosis). Scar tissue is typically not as flexible as healthy tissue. Therefore, when fibrosis occurs in the intestines, the scarring may narrow the width of the passageway (lumen) of the involved segments of the bowel. These constricted areas are called strictures. The strictures may be mild or severe, depending on how much they block the contents of the bowel from passing through the narrowed area. Clinical signs/symptoms of Crohn's disease can include but are not limited to: cachexia, weight loss, poor growth, abdominal pain, draining fistulae, rectal prolapse and dehydration.

In certain embodiments, an inflammatory hepatic disease or disorder. For example, an inflammatory hepatic disease or disorder is selected from the group consisting of autoimmune hepatitis, hepatic cirrhosis, and biliary cirrhosis.

Pharmaceutical Compositions and Administration

The present invention contemplates pharmaceutical preparations comprising an agent that binds to denatured collagen (e.g., collagen type I-IV), in particular denatured collagen type-IV, together with a pharmaceutically acceptable carrier. Polypeptides of the invention may be administered as part of a pharmaceutical composition. The compositions should be sterile and contain a therapeutically effective amount of the polypeptides in a unit of weight or volume suitable for administration to a subject.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethyl amine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an inflammation inhibiting amount or a fibrosis inhibiting amount of an denatured collagen antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

These compositions can be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous antagonist polypeptide solution, and the resulting mixture can then be lyophilized. The infusion solution can be prepared by reconstituting the lyophilized material using sterile Water-for-Injection (WFI).

The compositions can be administered in effective amounts. The effective amount will depend upon the mode of administration, the particular condition being treated, and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

The dosage ranges for the administration of the denatured collagen antagonist depend upon the form of the antagonist, and its potency, as described further herein, and are amounts large enough to produce the desired effect in which inflammation or fibrosis and the disease symptoms mediated by inflammation or fibrosis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage also can be adjusted by the individual physician in the event of any complication.

A therapeutically effective amount is an amount of denatured collagen antagonist sufficient to produce a measurable inhibition of inflammation or fibrosis in the tissue being treated. Fibrosis can be measured by various non-invasive methods including palpation, ocular examination, retinal examination, X-ray, ultrasound, MRI, as well as invasive methods such as biopsy with histopathological examination and molecular marker analysis, endoscopy, isotope incorporation and gamma scintigraphy. Inflammation can be measured noninvasively by palpation, ocular examination, retinal examination, assessment of body and tissue temperature, and functional evaluation of blood flow in tissue by ultrasound or MRI as well as invasively by methods such as biopsy with histopathological examination and molecular marker analysis, endoscopy, isotope incorporation and gamma scintigraphy. All above methods of measurement are used in conjunction with assessment of clinical parameters for function of the affected tissue.

In specific embodiments, inflammation is measured as described in the Examples (e.g., CAM assays, or by measuring macrophage marker staining). In other embodiments, fibrosis is measured using a bleomycin mouse model, or by measuring collagen synthesis.

A therapeutically effective amount of an agent of this invention in the form of a monoclonal antibody is typically an amount such that when administered in a physiologically tolerable composition is sufficient to achieve a plasma concentration of from about 0.01 microgram (ug) per milliliter (mL) to about 10 ug/mL, preferably from about 1 ug/mL to about 5 ug/mL, and usually about 5 ug/mL. Stated differently, the dosage can vary from about 0.5 mg/kg to about 100 mg/kg, preferably from about 0.5 mg/kg to about 50 mg/kg (e.g., 0.5, 1, 2, 3, 5, 10, 12, 15, 20, 25, 30, 35, 40, 45, 50 mg/kg) in one or more dose administrations daily, for one or several days. In one embodiment, the antibody dose is 0.5, 1, 5, 10, 15, 20, or 25 mg/kg.

Where the agent is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

A therapeutically effective amount of a denatured collagen antagonist of this invention in the form of a polypeptide, or small molecule, is typically an amount of polypeptide such that when administered in a physiologically tolerable composition is sufficient to achieve a plasma concentration of from about 0.1 microgram (ug) per milliliter (mL) to about 200 ug/mL, or from about 1 ug/mL to about 150 ug/mL. Based on a polypeptide having a mass of about 500 grams per mole, in one embodiment, the plasma concentration in molarity is from about 2 micromolar (uM) to about 5 millimolar (mM) or from about 100 uM to 1 mM polypeptide antagonist. In other embodiments, the doses of small peptides range from about 500 mg/Kg to about 1.0 g/kg (e.g., 500, 600, 700, 750, 800, 900, 1000 mg/kg).

The agents of the invention can be administered parenterally by injection or by gradual infusion over time. In other embodiments, agents are administered intravenously, intraperitoneally, intramuscularly, subcutaneously, intracavity, transdermally, topically, intraocularly, orally, intranasally, and can be delivered by peristaltic means. In one particular embodiment, an agent of the invention is locally delivered to a site of inflammation or fibrosis.

In one embodiment, a therapeutic compositions containing an agent of this invention are administered in a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Kits

The invention provides kits for altering the activity of one or more types of inflammatory cells. In one embodiment, the kit detects provides an agent that binds denatured collagen type I-IV (e.g., denatured collagen type-IV), wherein the agent alters the activity of one or more types of inflammatory cells, and instructions for use. Preferably, the agent alters inflammatory infiltration of a tissue or organ.

In other embodiments, the kit comprises a sterile container which contains the antagonist; such containers can be boxes, ampules, bottles, vials, tubes, bags, pouches, blister-packs, or other suitable container form known in the art. Such containers can be made of plastic, glass, laminated paper, metal foil, or other materials suitable for holding agents as described herein. Preferably, the kit further comprises any one or more of reagents described or useful in the methods and compositions herein.

In other embodiments, the instructions include at least one of the following: methods for using the enclosed materials for the treatment or prevention of inflammation; methods for using the enclosed materials for the treatment or prevention of fibrosis; precautions; warnings; indications; clinical or research studies; and/or references. The instructions may be printed directly on the container (when present), or as a label applied to the container, or as a separate sheet, pamphlet, card, or folder supplied in or with the container.

This invention is further illustrated by the following examples, which should not be construed as limiting. All documents mentioned herein are incorporated herein by reference.

EXAMPLES

Example 1. CLK-Peptide Inhibited Eosinophillic Inflammatory Cell Infiltration

Figure 1B:
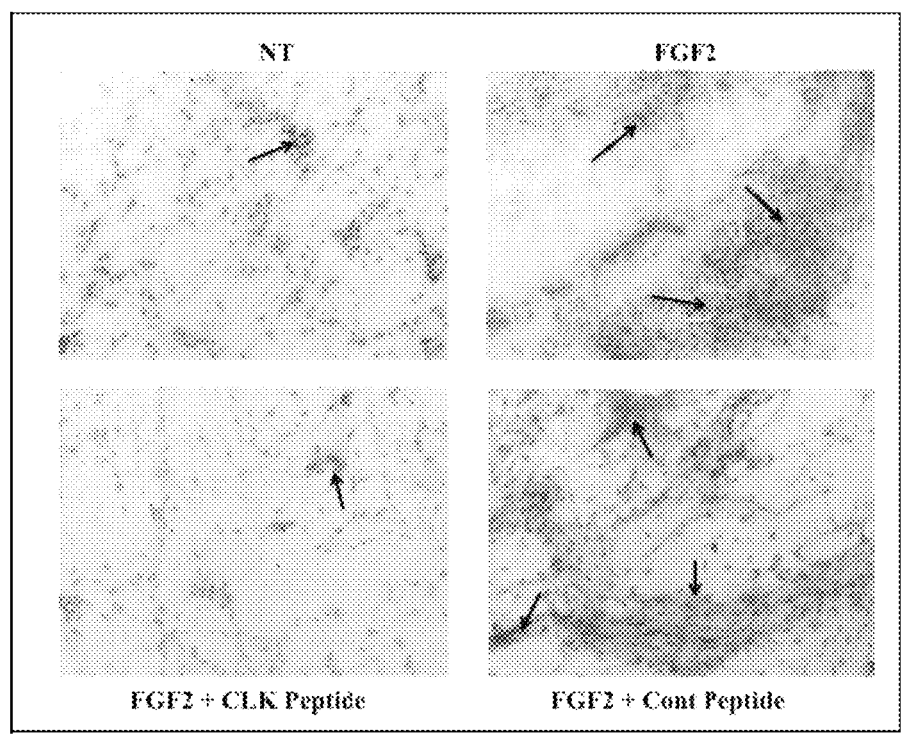

The Chick Chorioallantoic Membrane (CAM) model is a well-established in vivo model to examine a variety of complex biological processes, such as angiogenesis, tumor growth as well as inflammation. Investigators routinely use the CAM assay to examine the effects of various compounds and bio-implants on inflammation. In a first set of experiments, an inflammatory response was induced by physically separating the CAM from the shell membrane in the absence of cortisone acetate, and stimulating the CAM tissue with FGF-2 to induce a robust inflammatory response. The CLK or control peptides were then applied topically to the CAMs. At the end of a three-day incubation period the CAM tissues were removed and analyzed. As shown in FIG. 1A (Top left), untreated CAM tissues exhibited minimal if any tissue thickening surrounding the central filter disc. In contrast, bFGF (FGF-2) potently induced a strong inflammatory response (Top right) as indicated by the robust thickening of CAM, which begins to overlap and partially cover the central area of the filter disc (Arrows). Similar results are noted under control peptide treated conditions (Bottom left). Importantly, treatment with CLK-peptide (250 ug/day) dramatically reduced the overall levels of inflammation (Bottom right) as compared to either bFGF-2 alone (Top right) or control peptide (Bottom left). At the end of a three-day incubation period the CAM tissues were removed and analyzed. Resulting tissues were stained by hemotoxylin and eosin (H & E) and examined histologically. As shown in FIG. 1B (Top left), few eosinophillic infiltrates were observed in the untreated CAM tissues (Arrow). In contrast, FGF-2 potently induced a strong inflammatory response (Top right) as indicated by the robust infiltration of the eosinophillic (pink) infiltrates (arrows). These results showed that treatment with CLK-peptide dramatically reduced the overall levels of inflammatory infiltrates (Bottom left) as compared to either bFGF-2 alone (Top right) or control peptide (Bottom right).

To quantify the relative impact of the CLK-peptide on inflammation, the percentage of the individual CAMs from two independent experiments (FIGS. 1C and D) that exhibited strong positive inflammation was determined. Strong positive inflammation was scored as those CAMs where the CAM tissue was thickened and partially covered the central area of the filter disc. As shown in FIGS. 1C and D, the CLK peptide potently reduced the number of CAMs (percentage) exhibiting thickening (inflammation) as compared to either control peptide or bFGF treated CAMs. These surprising findings indicate that the cryptic epitope recognized by CLK-peptide likely regulates infiltration of eosinophillic infiltrates. Moreover, these studies indicate that targeting a cryptic collagen epitope is useful for the treatment of diseases and disorders associated with inflammation and fibrosis.

Example 2. Macrophages Adhere to the CLK/HU177 Cryptic Epitope

Figure 2:
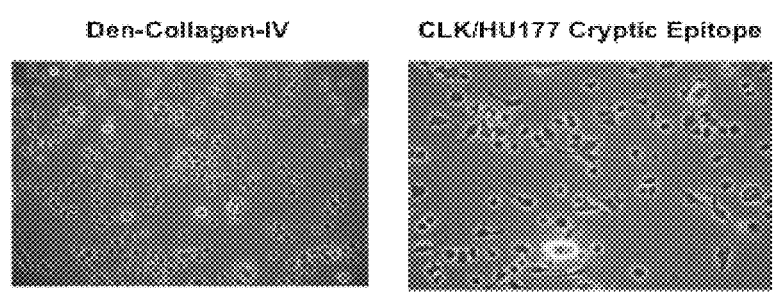
FIG. 2 includes two micrographs that show murine macrophage attachment to the CLK/HU177 cryptic collagen epitope. Culture plates were coated with either (A) denatured (den) collagen-IV or (B) the CLK/HUI77 cryptic epitope (16-mer OGAKGLPGPOGPOGPY SEQ ID NO: 1, where 0 represents hydroxylated prolines. Isolated primary murine peritoneal macrophages ($1 \times 10^5$) were seeded on the coated wells in adhesion buffer and allowed to attach for 45 minutes. Photos were taken at a magnification of 200×.

Macrophages represent one of many different inflammatory cell type that are thought to contribute to inflammation and fibrosis. To determine whether primary murine macrophages have the capacity to adhere and bind to denatured collagen, peritoneal macrophages were collected and seeded on denatured collagen type-IV-coated plates. As shown in FIG. 2A (Left panel), macrophages attached to denatured collagen-IV. To more specifically examine the ability of macrophages to interact with the CLK/HU177 cryptic site, cells were seeded on wells coated with the specific CLK/HU177 epitope and allowed to attach. As shown in FIG. 2B (Right panel), macrophages not only attached, but also began to spread on the CLK/HU177 cryptic epitope. These finding suggest that primary macrophages have the ability to bind to CLK/HU177 cryptic site exposed within collagen type-IV.

The CLK/HU177 cryptic epitope regulates endothelial cell behavior in vitro and angiogenesis in vivo, and thus provides one potential cellular mechanism that contributes to the ability of the CLK/HU177 epitope to regulate tumor progression (Cretu A., et al. Clin. Cancer. Res. 2007). Interestingly, a number of important studies have provided evidence that bone marrow-derived cells, such as macrophages, are actively recruited to sites of angiogenesis, tumor growth and metastasis and may play functional roles in regulating tumor progression (Pollard, J. W. Nat. Rev Immunol. 2009; Wycoff, J. B. Cancer Res. 2007; Bingle, L. J Pathol. 2002). Some studies have estimated that macrophage infiltration of tumors occurs in nearly 80% of cancers (Bingle, L. J Pathol. 2002). Elevated levels of macrophage infiltration of malignant tumors often correlates with poor prognosis (Torisu, H., Int. J. Cancer 2000; Prost. Lip. Med. 83: 320-328. 2007).

To gain access to sites of angiogenesis and tumor growth, macrophages must adhere to, invade and migrate through both basement membranes and the interstitial matrix. Macrophages have been shown to be a major source of pro-angiogenic factors, such as VEGF and matrix altering proteases such as MMP-9, thereby contributing to tumor progression (Murdoch, C., Nat. Rev. Cancer. 2008; Nakamura, T., Neoplasia. 2007). Studies have indicated that MMP-9 plays an important role in exposing cryptic collagen epitopes at sites of tissue invasion (Hangai. M., Am. J. Pathol. 2002; Gagne, P. J., Am. J. Pathol. 2005). Given these findings, coupled with the known role of macrophages in tissue remodeling, localized exposure of the CLK/HU177 cryptic epitope may provide a selectively expressed cryptic ECM ligand used by macrophages to facilitate their infiltration into tumors.

While some studies have suggested that macrophages can help reduce tumor growth, many other studies have indicated macrophages may promote tumor progression (Mytar, B., Anticancer Res. 2008; Ono, M. Cancer Sci. 2008; Lewis, C. E., Cancer Res. 2006). In fact, studies suggest that depletion of macrophages reduces angiogenesis, tumor growth, and metastasis in certain tumor types (Mytar, B., Anticancer Res. 2008; Ono, M. Cancer Sci. 2008; Lewis, C. E., Cancer Res. 2006). In addition, selective inhibition of M-CSF (Macrophage Colony Stimulating Factor) can inhibit pathological angiogenesis in vivo (Kubota, Y., J. Exp. Med.). Moreover, recent studies also suggest that macrophages may incorporate into angiogenic vessels (Kim Am J Pathol. 2009).

Given these findings, the present inventors sought to determine whether macrophages might utilize the CLK/HU177 cryptic collagen epitope to infiltrate into malignant tumors. The findings suggest that macrophages interact with the CLK/HU177 cryptic epitope and that a function blocking peptide directed to this cryptic site inhibits macrophage binding. These novel results are consistent with the CLK/HU177 cryptic epitope regulating tumor progression by promoting macrophage infiltration into malignant tumors.

Figure 3:
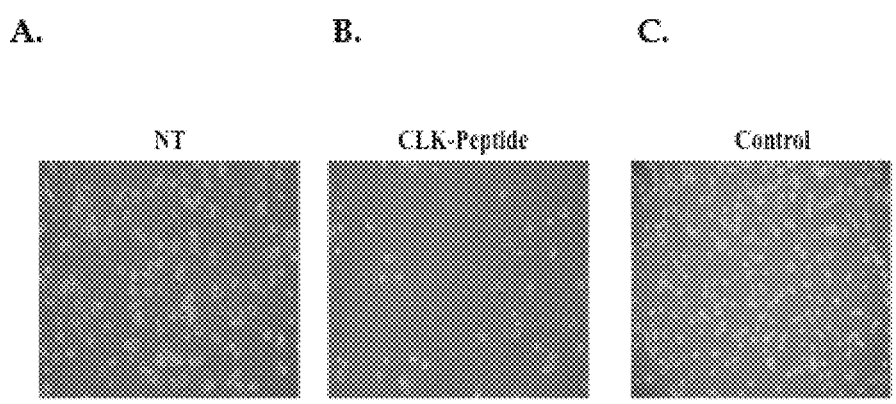
FIG. 3A, FIG. 3B, and FIG. 3C are photomicrographs showing that the CLK-peptide inhibits macrophage attachment to the CLK/HU177 cryptic collagen epitope. Culture plates were coated with the CLK/HUI77 cryptic epitope (OGAKGLPGPOGPOGPY (SEQ ID NO: 1)), where 0 represents hydroxylated prolines. Macrophages ($1 \times 10^5$) were seed on the coated wells in the presence (100 μg/m) or absence of CLK or control peptide and allowed to attach. Photos were taken at a magnification of 100×.

Example 3. Synthetic Function Blocking Peptide (CLK-Peptide) Directed to the CLK/HU177 Cryptic Epitope Reduces Macrophage Adhesion Given that the ability of macrophages to interact with damaged and denatured collagen is likely to play a role in their ability to localize to sites of tissue damage, a next set of experiments examined whether the synthetic peptide, which specifically binds to the CLK/HU177 cryptic epitope, inhibited macrophage adhesion in vitro. Culture plates were coated with the CLK/HU177 cryptic epitope as described above, and macrophages were allowed to bind in the presence or absence of the function blocking CLK peptide. As shown in FIG. 3A, macrophages readily attached to the immobilized cryptic collagen epitope. In contrast, macrophage adhesion was reduced (FIG. 3B) in the presence of the CLK-peptide as compared to no treatment (FIG. 3A) or control (FIG. 3C). These studies indicate that specifically targeting the CLK/HU177 cryptic epitope with a synthetic peptide inhibited macrophage adhesion to the CLK/HU177 cryptic site.

Figure 4:
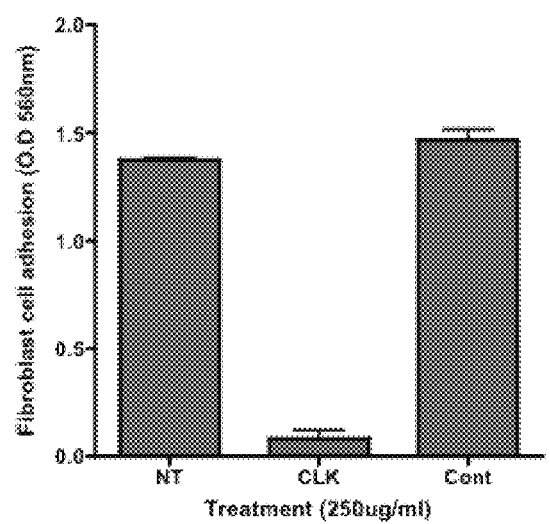
FIG. 4 is a graph showing that elevated levels of collagen type-I were detected in conditioned medium from fibroblasts attached to denatured collagen type-IV as compared to native collagen type-IV.

Example 4. Synthetic Function Blocking Peptide (CLK-peptide) Directed to the CLK/HU177 Cryptic Epitope Inhibits Fibroblast Cell Adhesion to Denatured Collagen Fibrosis involves the infiltration of activated fibroblasts, which secrete elevated levels of the collagen that forms fibrotic tissue. To determine whether the CLK-peptide might inhibit interactions of fibroblasts with denatured collagen-IV in vitro, culture plates were coated with denatured collagen type-IV, as described above, and rat fibroblasts were allowed to bind in the presence or absence of the function blocking CLK-peptide or a nonspecific control peptide. As shown in FIG. 4, fibroblasts readily attached to the immobilized denatured collagen. In contrast, fibroblast adhesion was dramatically inhibited in the presence of the CLK-peptide. The control peptide had little if any effect on fibroblast adhesion. These studies indicate that specifically targeting the CLK/HU177 cryptic epitope with a synthetic peptide inhibited interaction and infiltration of collagen secreting fibroblast into areas of tissue damage.

Figure 5:
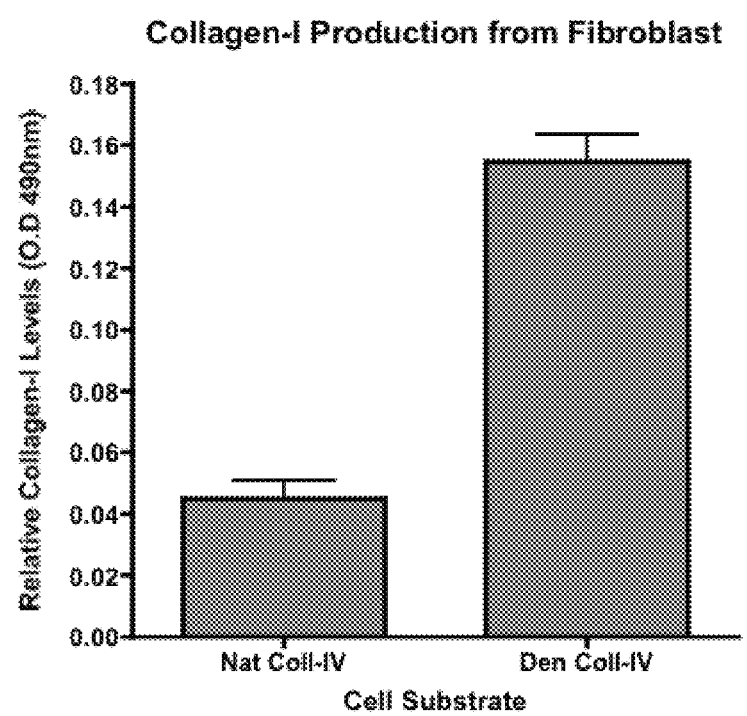
FIG. 5 is a graph showing that the CLK-peptide inhibited fibroblast cell adhesion to denatured collagen. Culture plates were coated with denatured collagen-IV (10 ug/ml). Rat fibroblasts were resuspended in the presence (250 μg/ml) or absence of CLK peptide (LKQNGGNFSL (SEQ ID NO: 4)) or control peptide (RYNEVKKKM (SEQ ID NO: 5)). Cells were allowed to attach for 30 minutes and stained with crystal violet. Data bars represent the mean OD+/−S.D. derived from eluted cell associated crystal violet.

Example 5: Fibroblast Interaction with Denatured Collagen-IV Results in Enhanced Collagen Production During inflammation and fibrosis, tissue damage is thought to result in elevated levels of proteolytic enzymes, which can denature a variety of forms of collagen. Importantly, a pathological hallmark of fibrosis is the increased expression and accumulation of matrix proteins, such as collagen type-I and -IV by fibroblast and other inflammatory cell types, which largely replaces the normal tissue structure. To determine whether the expression of collagen type-I was altered in fibroblasts interacting with normal intact collagen as compared to damaged or denatured collagen type-IV, equal numbers of rat fibroblast were resuspended in adhesion buffer and allowed to interact with culture plates coated with either intact native or denatured collagen-IV for 24 hours. Conditioned medium from each condition was then collected and the relative level of collagen type-I was examined by solid phase ELISA. As shown in FIG. 5, elevated levels of collagen type-I were detected in conditioned medium from fibroblasts attached to denatured collagen type-IV as compared to native collagen type-IV. These experiments suggest that fibroblast interactions with a cryptic epitope exposed within collagen type-IV may result in enhanced expression of collagen type-I.

Figure 6:
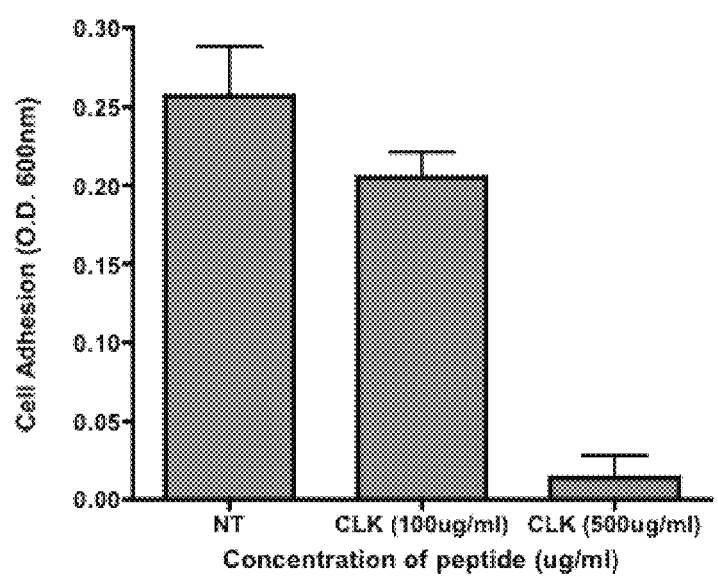
FIG. 6 is a graph showing that fibroblasts readily attached to immobilized denatured collagen. In contrast, fibroblast adhesion was dramatically inhibited in the presence of the CLK-peptide while the control peptide had little, if any, effect.

Example 6: CLK-peptide Inhibited Fibroblast Cell Adhesion to Denatured Collagen Type-I The cryptic collagen epitope recognized by the CLK-peptide is expressed within collagen type-I as well as collagen type-IV. Therefore to determine whether the CLK cryptic epitope may inhibit fibroblast cell adhesion to denatured collagen type-I, cell adhesion in vitro was examined as described above. Briefly, culture plates were coated with denatured collagen-I, and rat fibroblasts were allowed to bind in the presence or absence of the function blocking CLK-peptide or non-specific control peptide. As shown in FIG. 6, fibroblasts readily attached to the immobilized denatured collagen type-1. In contrast, fibroblast adhesion was dose dependently inhibited in the presence of the CLK-peptide. These studies indicate that specifically targeting the CLK/HU177 cryptic epitope with a synthetic peptide may inhibit fibroblast interactions with collagen type-I as well as collagen type-IV.

Example 7: UVA Irradiation Exposed the HU177 Cryptic Collagen Epitope In Vitro and in Explanted Murine Skin It is well accepted that chronic solar irradiation to unprotected skin is a major risk factor for many forms of skin cancer including melanoma. Military personnel may be unavoidably subjected to prolonged high level exposure to solar irradiation due to the unique nature of the environments encountered during military operations. In this regard, the identification of pathological mechanisms that facilitate carcinogenesis as well as the development of novel strategies to prevent or reduce UV-induced skin damage, may lead to reductions in the incidence and progression of melanoma. Recent studies suggest that even acute UV exposure can result in structural and biomechanical changes in the physical properties of extracellular matrix (ECM) molecules, such as collagen, which represents nearly 90% of the ECM protein in skin. UV-mediated alterations in collagen structure may result from multiple mechanisms such as direct UV-induced oxidative damage from reactive oxygen species (ROS) and secondary proteolytic damage from UV-induced inflammatory cell infiltration. Collectively, these mechanisms and others may result in the accumulation of altered collagen within basement membranes and within the interstitial stroma of UV-exposed skin. UV irradiation is also known to promote pathological alterations within the epidermal and dermal layers of the skin including epidermal hyperplasia, inflammatory cell infiltration, enhanced angiogenesis and modulation of gene expression in resident cells such as fibroblasts, keratinocytes and melanocytes.

UV irradiation can lead to specific changes within the molecular structure of collagen that are thought to contribute to photodamage in skin, such as altered molecular cross-linking, changes in thermal stability and degradation of protein structure. It was recently found that acute UVA irradiation, but surprisingly not UVB, at a dose as low as 0.6 J/cm$^2$, may cause exposure of the HU177 cryptic collagen epitope in vitro and within full thickness explanted murine skin. These surprising findings are of particular significance given that UVA wavebands represent most of the solar wavelengths that penetrate to the earth surface, as compared to UVB wavebands, which represent a significantly lower proportion of solar irradiation, but which is thought to mediate much of the cellular and DNA damage associated with UV irradiation.

It has previously been shown that the HU177 cryptic collagen epitope plays a role in angiogenesis and melanoma tumor growth (Cretu, 2007; Pollard, 2009). A humanized Mab termed D93 directed to the HU177 cryptic site is currently being evaluated in a phase 1 clinical trial. Studies suggest no significant dose limiting toxicities in patients up to 25 mg/kg and importantly, evidence of anti-tumor activity has been observed. Based on these findings and results described herein suggesting that a small peptide antagonist (CLK-peptide) of the HU177 epitope sharply reduces macrophage cell adhesion to damaged collagen and may reduce inflammatory cell infiltration in vivo, UV irradiation may induce an acute and early biomechanical change in collagen structure (HU177 epitope exposure) that may facilitate the invasion of inflammatory cells through UVA-altered basement membranes and interstitial matrix. This enhanced inflammation and associated stromal reaction may represent an early event that promotes the creation of a melanoma permissive microenvironment over time. Further, treatment with antagonists of the HU177 epitope, prior to or after exposure to UV irradiation, can likely prevent or reduce localized infiltration of damaging inflammatory cells and the subsequent establishment of melanoma tumors within the skin.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

CITATIONS

The following documents are cited herein.

Tomasek J. J., Gabbiani G., Hinz B., Chaponnier C., Brown R. A. Myofibroblasts and mechano-regulation of connective tissue remodelling. Nat. Rev. Mol. Cell Biol. 2002; 3:349-363.

Friedman S. L. Mechanisms of disease: mechanisms of hepatic fibrosis and therapeutic implications. Nat. Clin. Pract. Gastroenterol. Hepatol. 2004; 1:98-105.

Cretu, A., Roth, M., Caunt, M., Akalu, A., Policarpio, D., Formenti, S., Gagne, P., Liebes, L., and Brooks, P C Inhibition of angiogenesis by disrupting endothelial cell interactions with the novel HU177 cryptic collagen epitope. Clin. Cancer. Res. 13: 3068-3078. 2007.

Pollard, J. W. Trophic macrophages in development and disease. Nat. Rev Immunol. 9: 259-270. 2009.

Kim, S-J., Kim, J-S., Papadopoulos, J., Kim, W., Maya, M., Zhang, F., He, J., Fan, D., Langley, R., Fidler, I. J. Circulating monocytes expressing CD31: implications for acute and chronic angiogenesis.

Wyckoff, J. B., Wang, Y., Lin, E. Y., Goswanmi, S., Stanley, R. E., Segall, J. E., Pollard, J. W., Condeelis, J. Direct visualization of macrophages-assisted tumor cell intravasation in mammary tumors. Cancer Res. 67: 2649-2656. 2007.

Bingle, L., Brown, N. J., Lewis, C. E. The role of tumor associated macrophages in tumor progression: implications for anti-cancer therapies.

Torisu, H., Ono, M., Kiryu, H., Fume, M., Ohmoto, Y., Nakayama, J., Nishioka, Y., Sone, S., Kuwano, M. Macrophage infiltration correlates with tumor stage and angiogenesis in human malignant melanoma: possible involvement of TNFa and IL-1a. Int. J. Cancer. 85: 182-188. 2000.

Expression of cyclo-oxygenase-2 in macrophages associated with cutaneous melanoma at different stages of progression. Prost. Lip. Med. 83: 320-328. 2007.

Murdoch, C., Muthana, M., Coffelt, S. B., Lewis, C. E. Nat. Rev. Cancer. 8: 618-631. 2008.

Nakamura, T., Kuwai, T., Kim, J-S., Fan, D., Kim, S-J., Fidler, J. I. Stromal metalloproteinase-9 is essential to angiogenesis and progressive growth of orthotopic human pancreatic cancer in parabiont nude mice. Neoplasia. 9: 979-986. 2007.

Hangai. M., Kitaya, N., Chan, C. K., Xu, J., Kim, J. J., Ryan, S. J., and Brooks, P. C. MMP-9 Dependent Exposure of a Cryptic Migratory Control Site in Collagen is Required Prior to Retinal Angiogenesis. Am. J. Pathol. 161: 1429-1437. 2002.

Gagne, P. J., Tihonov, N., Li, X., Glaser, J., Qiao, J., Silberstein, M., Yee, H., Gagne, E., and Brooks, P. C. Temporal exposure of cryptic collagen epitopes within ischemic muscle during hindlimb reperfusion. Am. J. Pathol. 167: 1349-1359. 2005.

Mytar, B., Baj-Krzyworzeka, M., Stankiewicz, D., Zembala, M. Human monocytes both enhance and inhibit the growth of human pancreatic cancer in SCID mice. Anticancer Res. 28: 187-192. 2008.

Ono, M. Molecular links between tumor angiogenesis and inflammation: inflammatory stimuli of macrophages and cancer cells as targets for therapeutic strategy. Cancer Sci. 99: 1501-1506. 2008.

Lewis, C. E., Pollard, J. W. Distinct role of macrophages in different tumor microenvironments. Cancer Res. 66: 605-612. 2006.

Kubota, Y., Takubo, K., Shimizu, T., Ohno, H., Kishi, K., Shibuya, M., Saya, H., Suda, T. M-CSF inhibition, selectively targets pathological angiogenesis and lymphangiogenesis. J. Exp. Med.

Marconi, C., Bianchini, F., Mannini, A., Mugnai, G., Ruggieri, S., Calorini, L. Tumoral and macrophage uPAR and MMP-9 contribute to the invasiveness of B16 murine melanoma cells. Clin. Exp. Met. 25: 225-231. 2008.

Baek, Y-U., Hass, S., Hackstein, H., Bein, G., Hernandez-Santana, M., Lehrach, H., Sauer, S., Seitz, H. Identification of novel transcriptional regulators involved in macrophage differentiation and activation in U937 cells. BMC. Immunol. 10: 1-5. 2009.

Campana, L., Bosurgi, L., Bianchi, M. E., Manfredi, A. A., Rovere-Querini, P. Requirement of HMGB1 for stromal cell-derived factor-1/CXCL12-dependent migration of macrophages and dendritic cells. J. Leuk. Biol. 86: 1-6. 2009.

Pernasetti, F., Nickel, J., Clark, D., Baeuerle, P. A., Van Epps, D., Freimark, B. Novel anti-denatured collagen humanized antibody D93 inhibits angiogenesis and tumor growth: an extracellular matrixb ased therapeutic approach. Int. J. Oncol. 29: 1371-1379. 2006.

Shi, C., Simon, D. I. Integrin signals, transcription factors, and monocyte differentiation. Trend.

Cardiovas. Med. 16: 146-152. 2006.

Davis, G. E. The Mac-1 and p 150, 95 beta 2 integrin bind denatured proteins to mediate leukocyte cell substrate adhesion. Exp. Cell Res. 200: 242-252. 1992.

Jin, H., Su, J., Garmy-Susini, B., Kleeman, J., Varner, J. Integrin α4β1 promotes monocyte trafficking and angiogenesis in tumors. Cancer. Es. 66: 2146-2152. 2006.

Roth, J. M., Akalu, A., Zelmanovich, A., Policarpio, D., Ng, B., MacDonald, S., Formenti, S., Liebes, L., Brooks, P. C. Recombinant α2(IV)NC1 domain inhibits tumor cell extracellular matrix interactions, induces cellular senescence, and inhibits tumor growth in vivo. Am. J. Pathol. 166: 901-911. 2005.

What is claimed is:

1. A method of reducing solar ultraviolet radiation damage to an organ, wherein the organ is skin and the damage comprises inflammation, the method comprising administering to a subject a therapeutically effective amount of an antibody that binds an epitope of denatured collagen type IV comprising OGAKGLPGPOGPOGPY (SEQ ID NO: 1), wherein O represents a hydroxylated proline, wherein the solar ultraviolet radiation comprising UVA radiation.

2. The method of claim 1, wherein the antibody is administered prior to, concurrent with, or subsequent to exposure of the skin to solar ultraviolet radiation.

3. The method of claim 1, wherein the inflammation comprises inflammatory cell infiltration into the skin, and wherein the antibody reduces the inflammatory cell infiltration into the skin.

4. The method of claim 3, wherein the inflammatory cell is selected from the group consisting of: fibroblasts, monocytes, macrophages, neutrophils, and mast cells.

5. The method of claim 1, wherein the antibody reduces adhesion to extracellular matrix or basement membrane.

6. The method of claim 1, wherein the antibody reduces fibroblast cell adhesion to denatured collagen type IV.

7. The method of claim 1, wherein the antibody is a monoclonal antibody.

8. The method of claim 1, wherein the antibody is humanized.

9. The method of claim 1, wherein the subject does not have melanoma.

10. A method of reducing solar ultraviolet radiation-induced inflammatory cell infiltration into the skin, the method comprising administering to a subject who does not have melanoma a therapeutically effective amount of an antibody that binds an epitope of denatured collagen type IV comprising OGAKGLPGPOGPOGPY (SEQ ID NO: 1), wherein 0 represents a hydroxylated proline, wherein the solar ultraviolet radiation comprising UVA radiation, thereby reducing inflammatory cell infiltration into the skin.

* * * * *

SEQUENCE LISTING

```
<160> NUMBER OF SEQ ID NOS: 11

<210> SEQ ID NO 1
<211> LENGTH: 16
<212> TYPE: PRT
<213> ORGANISM: Unknown
<220> FEATURE:
<223> OTHER INFORMATION: Description of Unknown: Anti-denatured
      collagen type-IV epitope peptide
<220> FEATURE:
<221> NAME/KEY: MOD_RES
<222> LOCATION: (1)..(1)
<223> OTHER INFORMATION: Hydroxylated Pro
<220> FEATURE:
<221> NAME/KEY: MOD_RES
<222> LOCATION: (10)..(10)
<223> OTHER INFORMATION: Hydroxylated Pro
<220> FEATURE:
<221> NAME/KEY: MOD_RES
<222> LOCATION: (13)..(13)
<223> OTHER INFORMATION: Hydroxylated Pro
```

```
<400> SEQUENCE: 1

Pro Gly Ala Lys Gly Leu Pro Gly Pro Pro Gly Pro Pro Gly Pro Tyr
1               5                   10                  15

<210> SEQ ID NO 2
<211> LENGTH: 4
<212> TYPE: PRT
<213> ORGANISM: Unknown
<220> FEATURE:
<223> OTHER INFORMATION: Description of Unknown: Anti-denatured
      collagen type-IV epitope peptide

<400> SEQUENCE: 2

Gly Leu Gly Pro
1

<210> SEQ ID NO 3
<211> LENGTH: 6
<212> TYPE: PRT
<213> ORGANISM: Unknown
<220> FEATURE:
<223> OTHER INFORMATION: Description of Unknown: Anti-denatured
      collagen type-IV epitope peptide

<400> SEQUENCE: 3

Gly Leu Gly Pro Gly Pro
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Lys Gln Asn Gly Gly Asn Phe Ser Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Leu Lys Gln Asn Gly Gly Asn Phe Ser Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Leu Lys Gln Asn Gly Gly Asn Phe Ser Leu Gly
1               5                   10

<210> SEQ ID NO 7
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 7

Ser Leu Lys Gln Asn Gly Gly Asn Phe Ser Leu Cys
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Gly Gly Cys Leu Lys Gln Asn Gly Gly Asn Phe Ser Leu Gly Gly
1               5                   10                  15

Lys

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Tyr Asn Glu Val Lys Lys Lys Met
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Gly Gly Cys Leu Lys
1               5

<210> SEQ ID NO 11
<211> LENGTH: 5
<212> TYPE: PRT
<213> ORGANISM: Unknown
<220> FEATURE:
<223> OTHER INFORMATION: Description of Unknown: Denatured
      collagen epitope peptide

<400> SEQUENCE: 11

Gly Leu Pro Gly Pro
1               5
```